US008900804B2

(12) United States Patent
Kamlot et al.

(10) Patent No.: US 8,900,804 B2
(45) Date of Patent: Dec. 2, 2014

(54) METHODS AND SOLUTIONS FOR TISSUE PRESERVATION

(75) Inventors: Andreas Kamlot, Concord, CA (US); Alfredo Trento, Malibu, CA (US); Lawrence Czer, Santa Monica, CA (US); Jennifer Pass, Newton, NJ (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 2094 days.

(21) Appl. No.: 11/575,900

(22) PCT Filed: Nov. 15, 2005

(86) PCT No.: PCT/US2005/041532
§ 371 (c)(1),
(2), (4) Date: Dec. 26, 2007

(87) PCT Pub. No.: WO2006/057876
PCT Pub. Date: Jun. 1, 2006

(65) Prior Publication Data
US 2008/0286745 A1 Nov. 20, 2008

Related U.S. Application Data

(60) Provisional application No. 60/630,118, filed on Nov. 22, 2004.

(51) Int. Cl.
*A01N 1/02* (2006.01)

(52) U.S. Cl.
CPC . *A01N 1/02* (2013.01); *A01N 1/021* (2013.01); *A01N 1/0226* (2013.01)
USPC ............................................. 435/1.1; 435/1.2

(58) Field of Classification Search
CPC .............................. A01N 1/021; A01N 1/0226
USPC ..................................................... 435/1.1, 1.2
See application file for complete search history.

(56) References Cited

U.S. PATENT DOCUMENTS

| | | | |
|---|---|---|---|
| 4,798,824 A | 1/1989 | Belzer et al. | |
| 4,879,283 A | 11/1989 | Belzer et al. | |
| 5,498,427 A * | 3/1996 | Menasche | 424/678 |
| 6,046,046 A | 4/2000 | Hassanein | |
| 6,140,123 A | 10/2000 | Demetriou et al. | |
| 6,485,959 B1 | 11/2002 | Demetriou et al. | |
| 2003/0049840 A1 | 3/2003 | Demetriou et al. | |
| 2004/0038192 A1 | 2/2004 | Brasile | |
| 2004/0058432 A1 | 3/2004 | Owen et al. | |

FOREIGN PATENT DOCUMENTS

WO 2006057876 A2 6/2006

OTHER PUBLICATIONS

Osbakken et al., "Isolated Cardiomyocytes in Conjunction with NMR Spectroscopy Techniques to Study Metabolism and Ion Flux", J. Biol. Chem. 267 (22) : 15340-15347 (1992).*
Hjoberg et al., "Hyperosmolarity reduces the relaxing potency of nitric oxide donors in guinea-pig trachea", British J. Pharmacology 127 : 391-396 (1999).*
Tsutsumi et al., "Cardia Transplantation Following a 24-h Preservation Using a Perfusion Apparatus", J. Surgical Research 96 : 260-267 (2001).*
Wicomb et al., "Orthotopic transplantation of the baboon heart after 20 to 24 hours preservation by continuous hypothermic perfusion with an oxygenated hyperosmolar solution", J. Thoracic Cardiovascular Surg. 83 : 133-140 (1982).*
Mainnemare et al., "Hypochlorous Acid and Taurine-N-Monochloramine in Periodontal Disease", J. Dental Research 83 (11) : 823-831 (2004).*
Okada et al., "Successful 24-Hour Rabbit Heart Preservation by Hypothermic Continuous Coronary Microperfusion With Oxygenated University of Wisconsin Solution", Annals of Thoracic Surgery 60 : 1723-1728 (1995).*
May et al., "Seven-digit Replantation: Digit Survival after 39 Hours of Cold Ischemia", Plastic and Reconstructive Surgery 78 (4) : 522-525 (1986).*
Schenkman, "Cardiac performance as a function of intracellular oxygen tension in buffer-perfused hearts", Am. J. Physiol. Heart Circ. Physiol. 281 : H2463-H2472 (2001).*
ViaSpan Cold Storage Solution, Product Insert (May 2002).
Michel et al., A Comparative Study of the Most Widely Used Solutions for Cardiac Graft Preservation During Hypothermia, The Journal of Heart and Lung Transplantation, (2002), pp. 1030-1039, 21(9).
Collins, G.M., What Solutions Are Best? Overview of Flush Solutions, Transplantation Proceedings, (1997), pp. 3543-3544, 29.
Lemasters et al., Reperfusion Injury After Liver Preservation For Transplantation, Annual Review of Pharmacology and Toxicology, (1997), pp. 327-338, 37.
Olthoff et al., Comparison of UW Solution and Euro-Collins Solutions For Cold Preservation of Human Liver Grafts, Transplantation, (Feb. 1990), pp. 284-290, 49(2).
Stein et al., Cardiac Preservation In Patients Undergoing Transplantation, Journal of Thoracic and Cardiovascular Surgery, (1991),pp. 657-665, 102.

(Continued)

*Primary Examiner* — Sandra Saucier
(74) *Attorney, Agent, or Firm* — Linda B. Huber; Nixon Peabody LLP

(57) ABSTRACT

Described herein are compositions and methods particularly useful in the medical arts. The compositions and methods may be used in connection with the preservation of a portion of a mammal, for example, tissues, organs, appendages, limbs, extremities, stem cells, myocytes, bone marrow, skeletal muscle as well as an array of other medical procedures, such as cardiac surgery, transplantation and/or preservation. In various embodiments, the inventive composition may be hyperoxygenated and be formulated to resemble the biochemistries of natural intracellular fluids. The inventive composition includes active ingredients to reduce ischemic, hypothermic and reperfusion injury during transplantation, thereby resulting in improved post-transplant graft function and quality, when used in connection with organ transplantation and storage procedures, for example cardiac transplantation.

29 Claims, No Drawings

(56) References Cited

OTHER PUBLICATIONS

Lawton et al., Myocardial Protection With Potassium-Channel Openers Is As Effective As St. Thomas Solution In The Rabbit Heart, The Annals of Thoracic Surgery, (1996), pp. 31-39, 62.
Lawton et al., Myocardial Protection In The Acutely Injured Heart: Hyperpolarizing Versus Depolarizing Hypothermic Cardioplegia, The Journal of Thoracic and Cardiovascular Surgery, (Mar. 1997), pp. 567-575, 113(3).
Hsu et al., Quantitative Effects Of Myocardial Edema On The Left Ventricular Pressure-Volume Relation. Influence Of Cardioplegia Osmolarity Over Two Hours Of Ischemic Arrest, Journal of Thoracic and Cardiovascular Surgery, (Oct. 1993), pp. 651-657, 106(4).
Sade et al., A Prospective Randomized Study Of Hydroxyethel Starch, Albumin, and Lactated Ringer's Solution As Priming Fluid For Cardiopulmonary Bypass, Journal of Thoracic and Cardiovascular Surgery, (1985), pp. 713-722, 89.
Custodiol HTK Solution, Product Insert, (May 2004).
Martou, G. et al. Development of an in vitro model for study of the efficacy of ischemic preconditioning in human skeletal muscle against ischemia-reperfusion injury. Journal of Applied Physiology. (2006). 101:1335-1342.
Oguma, F. et al. Role Played by Oxygen in Myocardial Protection with Crystalloid Cardioplegic Solution. The Annals Thoracic Surgery. (1986). 42(2):172-179.
Oppell, L.M. et al. Effect of pH Shifts Induced by Oxygenating Crystalloid Cardioplegic Solutions. The Annals of Thoracic Surgery. (1991). 52:903-907.
PCT/US2005/041532 IPRP dated May 22, 2007.
PCT/US2005/041532 Written Opinion dated Aug. 17, 2006.

\* cited by examiner

METHODS AND SOLUTIONS FOR TISSUE PRESERVATION

This application is the National Phase of International Application PCT/US05/41532, filed Nov. 15, 2005, which designated the U.S. and that International Application was published under PCT Article 21(2) in English. This application also includes a claim of priority under 35 U.S.C. §119(e) to U.S. Provisional Patent Application No. 60/630,118, filed Nov. 22, 2004.

FIELD OF THE INVENTION

The invention relates to compositions and methods useful in the medical arts. In particular, the inventive composition may be used as an improved cardiac storage solution in connection with heart transplantation procedures, open-heart surgery, and preservation and/or transplantation of various other portions of a mammal, such as tissues, organs, appendages, limbs, extremities, bone marrow, skeletal muscle, stem cells and myoctyes.

BACKGROUND OF THE INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

There are approximately 2,500 heart transplants performed every year. A significant obstacle to successful heart transplantation is the limited tolerated ischemia time of the heart to about six hours with currently available preservation methods and solutions. This time frame significantly restricts the size of the geographic region from which a donor organ can transported before the viability of the donor organ for transplantation is compromised. Graft quality also decreases with prolonged storage time, and various studies have shown that suboptimal quality of a heart during transplantation is associated with increased risk of organ rejection in the postoperative period.

A number of transplantation preservation solutions are known in the art. See, e.g., P. Michel et al., "*A comparative study of the most widely used solutions for cardiac graft preservation during hypothermia,*" *J. Heart Lung Transplant.*, 21(9):1030-39 (2002). More than ten different preservation solutions are already in clinical use. Id. Moreover, there are several different solutions in use that are so-called "intracellular solutions." Id. Examples of "intracellular solutions" include University of Wisconsin (e.g., "UW," "Belzer™" or "Viaspan®") solution, the most commonly-used formulation, histidine-tryptophan-ketoglutarate (e.g., "HTK," "Bretschneider's" or "Custodiol®") solution, Stanford ("STF") solution, and Eurocollins ("EC") solution. See, e.g., G. M. Collins, "*What solutions are best? Overview of flush solutions,*" *Transplant. Proc.*, 29:3543-44 (1997), D. G. Stein et al., "*Cardiac preservation in patients undergoing transplantation. A clinical trial comparing University of Wisconsin solution and Stanford solution,*" *J. Thorac. Cardiovasc. Surg.*, 102:657-665 (1991), and D. T. Hsu et al., "*Quantitative effects of myocardial edema on the left ventricular pressure-volume relation. Influence of cardioplegia osmolarity over two hours of ischemia arrest,*" *J. Thorac. Cardiovasc. Surg.*, 106:651-657 (1993).

There is a need in the art for an improved cardiac transplantation solution. In particular, there is a need for a solution that enables the prolonged storage of an organ, such as a heart, for transplantation. By prolonging the tolerable ischemia time of an organ graft, the geographic region from which a donor organ can transported before the viability of the donor organ for transplantation is compromised may be markedly expanded. This, in turn, may improve organ transplantation quality and increase the number of potential donors.

SUMMARY OF INVENTION

This invention relates to methods and compositions to preserve a portion of a mammal, for example, tissues, organs, appendages, limbs, extremities, stem cells, myocytes, bone marrow and skeletal muscle. In various embodiments of the present invention, the methods and compositions may be used to improve the outcome after organ transplantation procedures, such as cardiac transplantation procedures.

In various embodiments the inventive composition may include a hyperoxygenated solution to preserve the tissues, organs, appendages, limbs, extremities, stem cells, myocytes, bone marrow and skeletal muscle. Further embodiments of the inventive composition may include active ingredients to reduce ischemic, hypothermic and reperfusion injuring during transplantation, thus resulting in improved post-transplant graft function and quality.

In alternate embodiments the inventive composition may be used with various tissue types for the preservation and/or transplantation of organs.

Further embodiments include methods to perfuse organs during the process of harvesting the organ and/or transplanting the organ.

Additional embodiments include methods to preserve an appendage, limb and/or extremity after a loss or detachment of the appendage, limb and/or extremity.

Other features and advantages of the invention will become apparent from the following detailed description.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994); and March, *Advanced Organic Chemistry Reactions, Mechanisms and Structure* 4th ed., J. Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Mammal" as used herein refers to any member of the class Mammalia, including, without limitation, humans and non-human primates such as chimpanzees, and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be including within the scope of this term.

"Hyper-oxygenate" water as used herein refers to having an amount of oxygen dissolved in water that is greater than an amount of oxygen that is dissolved in water at standard temperature and atmospheric pressure ("STP").

"Biochemistry of natural intracellular fluids" as used herein refers to the various electrolyte concentrations of the fluids that surround the target organ, for example, the natural intracellular fluid in cardiac tissue or the natural intracellular fluid in liver tissue, etc.

"Appendage" as used herein refers to a body part or organ that is joined to the trunk of the body. "Limb" as used herein refers to a body part that may be used for locomotion or grasping. "Extremity" as used herein refers to an outlying body part. Examples include but are not limited to an arm, leg, hand, foot, finger, toe, ear and nose. It is to be understood that these portions of the body may be classified as any one or more of the aforementioned terms.

The invention relates to compositions and methods useful in the medical arts. In various embodiments, the composition may be used to improve outcome after organ transplantation procedures; in particular, cardiac transplantation procedures. In accordance with various embodiments, the inventive composition includes active ingredients to reduce ischemic, hypothermic and reperfusion injury during transplantation; thereby resulting in improved post-transplant graft function and quality. The inventive composition may also be useful in the storage of myocytes or stem cells for cardiac or other applications. Further application includes the administration of the preservation solution during open-heart surgery, for example, with cardiopulmonary arrest.

In additional embodiments, the inventive composition may be used in connection with medical procedures related to a loss or detachment of an appendage, a limb or an extremity, for example, due to a traumatic injury, cosmetic surgery or reconstructive surgery. In these instances the appendage, limb or extremity, for example, an arm, a leg, a hand, a foot, a finger or a toe, may be placed and preserved in the inventive composition until a surgical reattachment procedure.

In alternate embodiments, the inventive composition may be used with variant tissue types and in connection with different medical procedures. By way of example, the inventive composition may be used in connection with the preservation and/or transplantation of any number of organs, such as kidney, liver, pancreas, eye, cornea, large intestine and small bowel; and with the preservation and/or transplantation of connective tissue such as skin cartilage, and bone. It may also be used as a base solution for lung or pulmonary preservation and/or transplantation, particularly when the inventive composition is supplemented with a protectant for lung surfactant and alveolar surface. The inventive composition may also be used as a perfusate to perfuse an organ during the process of harvesting and/or transplanting.

Further embodiments contemplate the use of the inventive composition for storage of bone marrow and skeletal muscle.

The concept underlying the inventive composition of the present invention is believed to run contrary to current practices in storing hearts for transplantation. Current practices typically involve ischemic (i.e., low oxygen) storage solutions used at hypothermic temperature (i.e., about 4° C.) and formulated at or about physiological pH (i.e., from about 7.2 to about 7.4) for storage of the donor organ. Ischemia is generally intended to minimize injury to cellular structures of the donor organ caused by highly reactive radicals that form in the presence of oxygen, such as superoxide radicals, hydroxyl radicals, nitric oxide radicals, and peroxynitrate radicals. See, e.g., J. J. Lemasters et al., "*Reperfusion injury after liver preservation for transplantation,*" Ann. Rev. Pharmacol. Toxicol., 37:327-38 (1997).

The inventive composition, on the other hand, includes a significant quantity of dissolved oxygen; indeed, it may be hyperoxygenated. In various embodiments, the inventive composition may exhibit an oxygen tension of from about 490 mmHg to about 590 mmHg. An oxygen tension of about 540 mmHg may be advantageous in accordance with particular embodiments of the present invention. Furthermore, the osmolarity of the inventive composition may be from about 325 mOsm to about 335 mOsm. An osmolarity of about 330 mOsm may be advantageous in accordance with particular embodiments of the present invention. This is believed to be in sharp contrast to currently available transplantation preservation solutions; some are oxygenated, but none are hyperoxygenated. Standard atmospheric oxygen content is less than about 160 mmHg, and under air dissolved oxygen content in aqueous solutions is significantly less; particularly as compared with the range of oxygen content in the inventive composition. See, e.g., U.S. patent publication Nos. 2004/0058432 and 2004/0038192, and Lemasters at 327-38. Moreover, the mere oxygenation of a transplantation solution is not described in the art, except perhaps under very specific circumstances of normothermic (i.e., at about 37° C.) storage without cardioplegia (i.e., without artificially induced heart arrest). See, e.g., U.S. Pat. No. 6,046,046.

Furthermore, the inventive composition may include one or more energy sources capable of being metabolized through the tricarboxylic acid (TCA) cycle; for example, glucose (with or without added insulin), glutamate, glutamine and/or glycine, either alone or in any suitable combination. Furthermore, the inventive composition may have a pH of from about 6.5 to about 7.0, which is markedly lower than currently available solutions. A pH of about 7.0 may be advantageous in accordance with particular embodiments of the present invention. While not wishing to be bound by any theory, it is believed that the maintenance energy provided by the one or more energy sources along with the relatively low pH protect against the loss of cell viability and membrane degradation. As the temperature of the donor organ is decreased from normal body temperature (at or around 37° C.) to the hypothermic temperature at which the donor organ may be maintained in the inventive composition (at or around 4° C.), adenosine triphosphate (ATP) shuttles are slowing, and thus the low pH is believed to inactivate proteolytic enzymes that would otherwise degrade membrane proteins at these lower temperatures (i.e., temperatures below about 20° C.).

The inventive composition may include glucose at a concentration of from about 19 mmol/L to about 21 mmol/L. A concentration of glucose of about 20 mmol/L may be advantageous in accordance with particular embodiments of the present invention. The inventive composition may include insulin at a concentration of from about 45 U/L to about 60 U/L. A concentration of insulin of from about 49 U/L to about 51 U/L may be advantageous in accordance with particular embodiments of the present invention. The inventive composition may include glutamine at a concentration of from about 1.7 mmol/L to about 3.0 mmol/L. A concentration of glutamine of from about 1.9 mmol/L to about 2.1 mmol/L may be advantageous in accordance with particular embodiments of the present invention. The inventive composition may include glutamate at a concentration of from about 0.8 mmol/L to about 1.5 mmol/L. A concentration of glutamate of from about 0.9 mmol/L to about 1.1 mmol/L may be advantageous in accordance with particular embodiments of the present invention. The inventive composition may include glycine at a concentration of from about 9.5 mmol/L to about 11.0 mmol/L. A concentration of glycine of from about 9.8 mmol/L to about 10.2 mmol/L may be advantageous in accordance with particular embodiments of the present invention.

Additionally, the inventive composition may include one or more radical scavengers and/or reductants to protect cellular structures against oxidative damage from radicals. By way of example, the inventive composition may include allopurinol and/or glutathione, either alone or in combination. Again, while not wishing to be bound by any particular theory, it is believed that the presence of one or more energy sources and the maintenance of aerobe metabolic activity in the presence of the oxygen that is dissolved in the inventive composition preserves the metabolic integrity of the cells of the donor organ and minimizes the generation of, and injury caused by, oxygen radicals to the same.

The inventive composition may include allopurinol at a concentration of from about 0.8 mmol/L to about 1.2 mmol/L. A concentration of allopurinol of about 1.0 mmol/L may be advantageous in accordance with particular embodiments of the present invention. The inventive composition may include glutathione at a concentration of from about 2.7 mmol/L to about 3.6 mmol/L. A concentration of glutathione of from about 2.9 mmol/L to about 3.2 mmol/L may be advantageous in accordance with particular embodiments of the present invention.

In various embodiments, the inventive composition may include active ingredients at an essential or near essential minimum. The use of active ingredients at an essential or near essential minimum aids in reducing the cost and complexity of manufacturing, yet the composition demonstrates superior function as compared to currently available products, as illustrated by the Examples herein described. It also imparts a relatively lower viscosity to the composition as compared with commercially available compositions typically used in connection with cardiac transplantation procedures. The relative viscosity of the inventive composition may be less than about 1.5 (relative to water). Relative viscosities of from about 1.0 to about 1.2 (relative to water) may be advantageous in accordance with particular embodiments of the present invention. Furthermore, as compared with currently available products, the inventive composition need not include calcium channel blockers, steroids and/or vitamins; although in alternate embodiments of the present invention, such items may be included. Again, while not wishing to be bound by any particular theory, it is believed that the low viscosity of the inventive composition combined with the osmolarity of from about 325 mOsm to about 335 mOsm, prevents osmotic stress on the cells, keeps the oxygen tension in the solution relatively high and more uniform, and allows the quicker introduction and removal with faster onset of organ protection as compared with the use of currently available transplantation solutions.

The inventive composition may also include various electrolytes, which may be formulated so as to resemble the biochemistry of natural intracellular fluids. Representative electrolytes include sodium chloride (NaCl), potassium chloride (KCl), magnesium sulfate ($MgSO_4$), and phosphate ($KH_2PO_4/K_2HPO_4$). The electrolytes may be present in the inventive composition at concentrations that approximate their respective concentrations in the natural intracellular fluid that the inventive composition is intended to mimic; for example, intracellular fluid in cardiac tissue in those embodiments of the instant invention wherein the inventive composition is for use in connection with cardiac transplantation or other procedures involving cardiac tissue (e.g., open heart surgery with cardiac arrest, cardiac arterial bypass graft surgery, etc.). Particularly for embodiments of the instant invention involving use of the inventive composition in cardiac procedures, the electrolytes may include sodium chloride (NaCl) at a concentration of from about 3.75 mmol/L to about 4.50 mmol/L; potassium chloride (KCl) at a concentration of from about 115 mmol/L to about 125 mmol/L; magnesium sulfate ($MgSO_4$) at a concentration of from about 2.1 mmol/L to about 2.8 mmol/L; and phosphate ($KH_2PO_4/K_2HPO_4$) at a concentration of from about 3.5 mmol/L to about 4.0 mmol/L. Concentrations of about 4.00 mmol/L of sodium chloride (NaCl), about 120 mmol/L of potassium chloride (KCl), about 2.4 mmol/L of magnesium sulfate ($MgSO_4$), and about 3.7 mmol/L of phosphate ($KH_2PO_4/K_2HPO_4$) may be advantageous in accordance with particular embodiments of the present invention. The respective concentrations of sodium chloride (NaCl) and potassium ($KH_2PO_4/K_2HPO_4$) cations, in particular, resemble intracellular concentrations, as opposed to extracellular concentrations, which are essentially the reverse. Therefore, the inventive composition falls within the category of so-called "intracellular solutions," as opposed to so-called "extracellular solutions." Once more, while not wishing to be bound by any particular theory, it is believed that this formulation prevents the physiological disruption of the cell membrane and allows the quicker introduction and removal with faster onset of organ protection.

The inventive composition may include adenosine, which may be present at a concentration of from about 2.5 mmol/L to about 4.0 mmol/L. Concentrations of adenosine of from about 2.9 mmol/L to about 3.1 mmol/L may be advantageous in accordance with particular embodiments of the present invention.

The inventive composition may include a buffer, such as HEPES (4-2-hydroxyethyl-1-piperazineethanesulfonic acid), an organic chemical buffer, which may be present at a concentration of from about 19 mmol/L to about 21 mmol/L. A concentration of HEPES of about 20 mmol/L may be advantageous in accordance with particular embodiments of the present invention.

EXAMPLES

The following examples demonstrate the preparation, use and efficacy of the inventive composition in connection with cardiac transplantation and preservation.

Example 1

Preparation of Cardiac Transplantation Preservation Solution

The cardiac transplantation solution is prepared by mixing each component thereof in distilled water. The media undergoes mechanical filter sterilization, oxygenation with 95% $O_2$ and 5% $CO_2$, pH and osmolarity adjustment Example 2

Harvest of Donor Organs from Experimental Animals

Nine rats in each experimental group underwent a standard method of harvesting the heart for transplantation. Briefly, each animal was anesthetized and the chest was opened. The blood vessels leading to the heart were clamped and the heart was arrested (i.e., cardioplegia) with a perfusion of cold solution. The heart was removed and placed in cold (4° C.) solution for preservation. Death occurred in the anesthetized donor animal once the heart was removed.

Example 3

Comparative Study of Donor Organ Function in Transplantation Preservation Solution The rat hearts were divided into groups based on different storage solutions and the length of cold preservation (i.e., 6, 8 or 10 hours of storage). Following the storage period, the hearts were attached to a Langendorff perfusion system, and physiological measurements of heart function were conducted over a period of 20 minutes. The results are illustrated in Table 1, below.

TABLE 1

Comparative Study of Inventive Composition and UW Solution

| Measurements | UW Mean ± SD | Inventive Composition Mean ± SD | $p < 0.05$ |
|---|---|---|---|
| Period 1 (0-5 minutes) | | | |
| HR1 | 170.7 ± 107.6 | 154.7 ± 72.3 | |
| Max-P1 | 14.5 ± 4.6 | 19.5 ± 9.0 | |
| EDP1 | 9.8 ± 3.1 | 8.2 ± 2.0 | |
| dP/dt1 | 241.9 ± 97.5 | 469.7 ± 297.3 | X |
| NdP/dt1 | 196.9 ± 57.7 | 398.0 ± 305.4 | X |
| PG1 | 4.8 ± 3.1 | 11.2 ± 8.5 | X |
| EF1 | 794.1 ± 681.5 | 1573.6 ± 1154.9 | X |
| Period 2 (5-10 minutes) | | | |
| HR2 | 270.0 ± 278.5 | 143.9 ± 61.2 | |
| Max-P2 | 14.5 ± 5.0 | 16.4 ± 5.2 | |
| EDP2 | 10.8 ± 3.9 | 8.1 ± 2.5 | X |
| dP/dt2 | 198.8 ± 56.9 | 337.7 ± 169.9 | X |
| NdP/dt2 | 166.4 ± 45.7 | 272.6 ± 115.8 | X |
| PG2 | 3.7 ± 2.5 | 8.3 ± 5.0 | X |
| EF2 | 720.7 ± 540.2 | 1170.2 ± 847.6 | |
| Period 3 (10-15 minutes) | | | |
| HR3 | 234.9 ± 208.6 | 164.9 ± 46.5 | |
| Max-P3 | 14.8 ± 5.7 | 14.6 ± 4.4 | |
| EDP3 | 10.3 ± 4.2 | 6.6 ± 3.2 | X |
| dP/dt3 | 205.0 ± 52.8 | 363.9 ± 180.4 | X |
| NdP/dt3 | 171.6 ± 36.7 | 318.6 ± 183.8 | X |
| PG3 | 4.6 ± 3.1 | 8.0 ± 4.7 | X |
| EF3 | 716.2 ± 361.5 | 1317.2 ± 881.7 | X |
| Period 4 (15-20 minutes) | | | |
| HR4 | 193.1 ± 132.1 | 179.3 ± 59.4 | |
| Max-P4 | 15.1 ± 6.5 | 15.9 ± 5.6 | |
| EDP4 | 9.1 ± 4.5 | 6.4 ± 3.4 | X |
| dP/dt4 | 237.4 ± 73.0 | 433.7 ± 201.2 | X |
| NdP/dt4 | 188.2 ± 50.8 | 383.1 ± 275.2 | X |
| PG4 | 6.0 ± 4.5 | 9.7 ± 5.7 | |
| EF4 | 830.9 ± 522.8 | 1783.0 ± 1345.3 | X |
| Period t (0-20 minutes) | | | |
| HR_t | 868.7 ± 698.2 | 642.8 ± 203.8 | |
| Max-P_t | 59.0 ± 19.5 | 66.3 ± 21.0 | |
| EDP_t | 39.9 ± 14.4 | 29.2 ± 9.6 | X |
| dP/dt_t | 883.1 ± 208.3 | 1605.0 ± 671.3 | X |
| NdP/dt_t | 723.0 ± 150.8 | 1372.4 ± 802.9 | X |
| PG_t | 19.1 ± 11.1 | 37.2 ± 20.0 | X |
| EF_t | 3061.9 ± 1781.2 | 5843.9 ± 3509.1 | X |

HR = heart rate (beats/min)
Max-P = maximum pressure (mmHg)
EDP = end diastolic pressure (mmHg)
dP/dt = maximum rate of pressure rise (mmHg/sec)
NdP/dt = maximum rate of pressure decline (mmHg/sec)
PG = pressure gradient (Max-P − EDP) (mmHg)
EF = ejection fraction (HR × PG)

As shown in Table 1, use of the inventive composition demonstrated significant (i.e., about 70% to about 130%) improvement over the UW solution; storage in the inventive composition resulted in greater ejection fraction (EF) from the left ventricle and greater pressure upslope (dP/dt) and pressure downslope (NdP/dt), compared to storage in University of Wisconsin (UW) solution. The improvements in EF, dP/dt and NdP/dt indicate greater strength and elasticity of the stored heart muscle using the inventive composition.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A method of preserving a portion of a mammal comprising:
   placing the portion of the mammal in contact with a preservation solution during storage, wherein the preservation solution comprises
   a quantity of water,
   an energy source capable of being metabolized through the tricarboxylic acid cycle comprising a quantity of glucose, a quantity of glutamate, a quantity of glutamine and a quantity of glycine,
   reductants comprising glutathione and allopurinol,
   electrolytes comprising sodium chloride, potassium chloride, magnesium sulfate, potassium phosphate ($KH_2PO_4/K_2HPO_4$),
   a quantity of dissolved oxygen, wherein the quantity of dissolved oxygen produces an oxygen tension of 490 mmHg to 590 mmHg,
   wherein the osmolarity of the solution is from 325 mOsm to 335 mOsm, the pH is from 6.5 to 7.0 and whereby the portion of the mammal is preserved during storage.

2. The method of claim 1, further comprising: maintaining the portion of the mammal in the preservation solution at a hypothermic temperature.

3. The method of claim 1, further comprising: maintaining the portion of the mammal in the preservation solution for a period of time of at least six hours during storage.

4. The method of claim 1, wherein the portion of the mammal is an organ.

5. The method of claim 4, further comprising: perfusing the organ with the preservation solution after storage.

6. The method of claim 4, wherein the organ is adapted for use in organ transplantation.

7. The method of claim 4, wherein the organ is selected from the group consisting of a kidney, a liver, a pancreas, a lung, a heart, an eye, a cornea, a large intestine and a small bowel.

8. The method of claim 5, wherein the organ is a heart positioned in a human during a surgical procedure.

9. The method of claim 1, wherein the portion of the mammal is connective tissue adapted for use in tissue transplantation.

10. The method of claim 9, wherein the connective tissue is selected from the group consisting of skin, cartilage, bone and bone marrow.

11. The method of claim 1, wherein the portion of the mammal is an appendage, a limb and/or an extremity.

12. The method of claim 11, wherein the appendage, the limb and/or the extremity is selected from the group consisting of an arm, a leg, a hand, a foot, a finger, a toe and combinations thereof.

13. The method of claim 1, wherein the portion of the mammal is skeletal muscle.

14. The method of claim 1, wherein the quantity of glucose is from about 19 mmol/L to about 21 mmol/L.

15. The method of claim 1, wherein the quantity of glutamate is from about 0.8 mmol/L to about 1.5 mmol/L.

16. The method of claim 1, where in the quantity of glutamine is from about 1.7 mmol/L to about 3.0 mmol/L.

17. The method of claim 1, wherein the quantity of glycine is from about 9.5 mmol/L to about 11.0 mmol/L.

18. The method of claim 1, wherein the solution further comprises a quantity of insulin.

19. The method of claim 18, wherein the quantity of glucose is from about 19 mmol/L to about 21 mmol/L and the quantity of insulin is from about 49 U/L to about 51 U/L.

20. The method of claim 1, wherein the allopurinol is present in an amount of from about 0.8 mmol/L to about 1.2 mmol/L.

21. The method of claim 1, wherein the glutathione is present in an amount of from about 2.7 mmol/L to about 3.6 mmol/L.

22. The method of claim 1, wherein the NaCl is present in an amount of from about 3.75 mmol/L to about 4.50 mmol/L.

23. The method of claim 1, wherein the KCl is present in an amount of from about 115 mmol/L to about 125 mmol/L.

24. The method of claim 1, wherein the $MgSO_4$ is present in an amount of from about 2.1 mmol/L to about 2.8 mmol/L.

25. The method of claim 1, wherein the $KH_2PO_4/K_2HPO_4$ is present in an amount of from about 3.5 mmol/L to about 4.0 mmol/L.

26. The method of claim 1, wherein the solution has a viscosity relative to water that is less than 1.5.

27. The method of claim 1, further comprising a quantity of adenosine.

28. The method of claim 27, wherein the quantity of adenosine is from about 2.5 mmol/L to about 4.0 mmol/L.

29. The method of claim 1, wherein the solution futher comprises 4-2-hydroxyethyl-1-piperazineethanesulfonic acid, present in an amount from about 20 mmol/L to about 21 mmol/L.

* * * * *